United States Patent
Shoham

(10) Patent No.: US 11,864,795 B2
(45) Date of Patent: Jan. 9, 2024

(54) THREE DIMENSIONAL ROBOTIC BIOPRINTER

(71) Applicant: MAZOR ROBOTICS LTD., Caesarea (IL)

(72) Inventor: Moshe Shoham, Hoshaya (IL)

(73) Assignee: MAZOR ROBOTICS LTD., Caesarea (IL)

( * ) Notice: Subject to any disclaimer, the term of this patent is extended or adjusted under 35 U.S.C. 154(b) by 793 days.

(21) Appl. No.: 16/500,347

(22) PCT Filed: Apr. 2, 2018

(86) PCT No.: PCT/IL2018/050384
§ 371 (c)(1),
(2) Date: Oct. 2, 2019

(87) PCT Pub. No.: WO2018/185755
PCT Pub. Date: Oct. 11, 2018

(65) Prior Publication Data
US 2021/0007778 A1    Jan. 14, 2021

Related U.S. Application Data

(60) Provisional application No. 62/480,455, filed on Apr. 2, 2017.

(51) Int. Cl.
*A61B 17/34* (2006.01)
*A61B 34/10* (2016.01)
(Continued)

(52) U.S. Cl.
CPC .......... *A61B 17/3468* (2013.01); *A61B 34/20* (2016.02); *A61B 34/30* (2016.02);
(Continued)

(58) Field of Classification Search
CPC .......... A61F 2002/30985; B33Y 30/00; A61B 34/35; A61B 34/77
See application file for complete search history.

(56) References Cited

U.S. PATENT DOCUMENTS 7,051,654 B2    5/2006  Boland et al.
7,875,324 B2    1/2011  Barron et al.
(Continued)

FOREIGN PATENT DOCUMENTS

CN    103462725    12/2013
CN    103655005    3/2014
(Continued)

OTHER PUBLICATIONS

Liu, Wanjun, et al. "Rapid continuous multimaterial extrusion bioprinting." Advanced materials 29.3 (2017): 1604630. (Year: 2017).*

(Continued)

*Primary Examiner* — Jacob J Cigna
(74) *Attorney, Agent, or Firm* — Sheridan Ross P.C.

(57) ABSTRACT

A minimally invasive system using a surgical robot as a three-dimensional printer for fabrication of biological tissues inside the body of a subject. A preoperative plan is used to direct and control both the motion of the robot and the robotic bio-ink extrusion. The robotic motion is coordinated with the ink extrusion to form layers having the desired thickness and dimensions, and use of different types of ink enables composite elements to be laid down. Such systems have a small diameter bio-ink ejecting mechanism, generally in the form of a piston driven cannula, enabling access to regions such as joints, with limited space. The robotic control is programmed such that angular motion takes place around a pivot point at the point of insertion into the subject.

(Continued)

The bio-inks can be stored in predetermined layers in the cannula to enable sequential dispensing from one cannula.

22 Claims, 6 Drawing Sheets

(51) Int. Cl.
| | |
|---|---|
| *A61B 34/20* | (2016.01) |
| *A61B 34/30* | (2016.01) |
| *A61B 34/32* | (2016.01) |
| *B33Y 10/00* | (2015.01) |
| *B33Y 30/00* | (2015.01) |
| *B33Y 50/02* | (2015.01) |
| *B33Y 80/00* | (2015.01) |

(52) U.S. Cl.
CPC .............. *A61B 34/32* (2016.02); *B33Y 10/00* (2014.12); *B33Y 30/00* (2014.12); *B33Y 50/02* (2014.12); *B33Y 80/00* (2014.12); *A61B 2034/107* (2016.02); *A61B 2034/2065* (2016.02); *A61B 2034/302* (2016.02)

(56) References Cited

U.S. PATENT DOCUMENTS

| | | | |
|---|---|---|---|
| 8,343,740 B2* | 1/2013 | Gonda | C12M 25/14 |
| | | | 435/284.1 |
| 9,626,989 B1 | 4/2017 | Guillemot et al. | |
| 10,046,091 B2* | 8/2018 | Hyde | A61L 27/3633 |
| 10,751,943 B2* | 8/2020 | Grbic | A61F 2/2415 |
| 10,888,428 B2* | 1/2021 | Hoelzle | B33Y 10/00 |
| 2003/0175410 A1 | 9/2003 | Campbell et al. | |
| 2011/0136162 A1* | 6/2011 | Sun | B01L 3/502761 |
| | | | 118/723 R |
| 2013/0123798 A1 | 5/2013 | Tsao et al. | |
| 2015/0037445 A1* | 2/2015 | Murphy | B29C 64/106 |
| | | | 425/131.1 |
| 2015/0084232 A1* | 3/2015 | Rutz | A61L 27/18 |
| | | | 435/325 |
| 2015/0158043 A1* | 6/2015 | Hart | B05D 3/14 |
| | | | 118/712 |
| 2015/0351896 A1* | 12/2015 | D'Lima | B33Y 80/00 |
| | | | 604/522 |
| 2016/0129155 A1 | 5/2016 | Lin et al. | |
| 2016/0288414 A1 | 10/2016 | Ozbolat et al. | |
| 2016/0374770 A1* | 12/2016 | Janik | A61B 34/20 |
| | | | 604/500 |
| 2017/0020630 A1 | 1/2017 | Johnson et al. | |
| 2018/0050550 A1* | 2/2018 | Batt | C23C 14/28 |
| 2019/0076257 A1* | 3/2019 | Dee | A61B 17/1635 |
| 2019/0275205 A1* | 9/2019 | D'Lima | A61M 5/14212 |
| 2020/0324469 A1* | 10/2020 | Zhang | B29C 64/106 |

FOREIGN PATENT DOCUMENTS

| | | |
|---|---|---|
| CN | 204092271 | 1/2015 |
| CN | 104688388 | 6/2015 |
| CN | 105751510 | 7/2016 |
| CN | 106361431 | 2/2017 |
| EP | 1278458 | 1/2003 |
| EP | 1414362 | 5/2004 |
| JP | 2015-163196 | 9/2015 |
| JP | 2016-501557 | 1/2016 |
| WO | WO 2010/064234 | 6/2010 |
| WO | WO 2015/118422 | 8/2015 |
| WO | WO 2015/142787 | 9/2015 |
| WO | WO 2017/080646 | 5/2017 |

OTHER PUBLICATIONS

Official Action for India Patent Application No. 201937040628, dated Jan. 13, 2022, 6 pages.
Official Action with English Translation for Japan Patent Application No. 2020-503107, dated Dec. 8, 2021, 17 pages.
Yaniv et al. "Needle-Based Interventions With the Image-Guided Surgery Toolkit (IGSTK): From Phantoms to Clinical Trials," IEEE Transactions on Biomedical Engineering, Apr. 2010, vol. 57, No. 4, pp. 922-933.
Extended Search Report for European Patent Application No. 18781604.6, dated Dec. 9, 2020, 13 pages.
International Search Report and Written Opinion prepared by the Israel Patent Office dated Jul. 9, 2018, for International Application No. PCT/IL2018/050384.
Cui et al. "Direct Human Cartilage Repair Using Three-Dimensional Bioprinting Technology," Tissue Engineering: Part A, 2012, vol. 18, No. 11 & 12, pp. 1304-1312.
Di Bella et al. "In situ handheld three-dimensional bioprinting for cartilage regeneration," Journal of Tissue Engineering for Regenerative Medicine, Mar. 2018, vol. 12, No. 3, pp. 611-621.
Hong et al. "3D bioprinting and its in vivo applications," Journal of Biomedical Materials Research Part B: Applied Biomaterials, Jan. 2018, vol. 106, No. 1, pp. 444-459.
O'Connell et al. "Development of the Biopen: a handheld device for surgical printing of adipose stem cells at a chondral wound site," Biofabrication, Mar. 2016, vol. 8, No. 1, 015019.
Rengier et al. "3D printing based on imaging data: review of medical applications," International Journal of Computer Assisted Radiology Surgery, Jul. 2010, vol. 5, No. 4, pp. 335-341.
Wang et al. "The trend towards in vivo bioprinting," International Journal of Bioprinting, 2015, vol. 1, No. 1, pp. 15-26.
Official Action with English Translation for China Patent Application No. 201880036057.3, dated Sep. 15, 2022, 25 pages.
Official Action with English Translation for Korea Patent Application No. 10-2019-7032312, dated Aug. 22, 2022, 12 pages.
Extended Search Report for European Patent Application No. 21203191.8, dated Apr. 19, 2022, 13 pages.

* cited by examiner

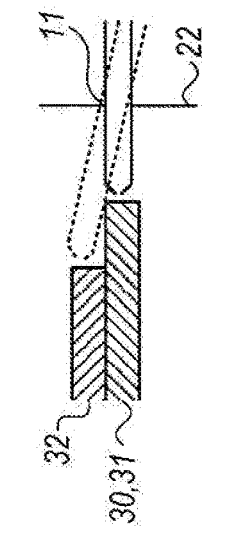
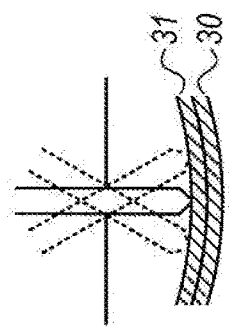
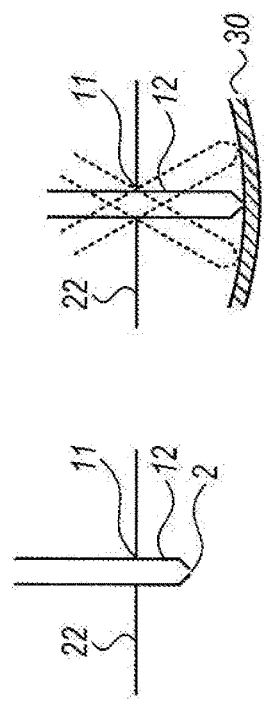

THREE DIMENSIONAL ROBOTIC BIOPRINTER

CROSS REFERENCE TO RELATED APPLICATIONS

This patent application is a U.S. National Stage of International Patent Application No. PCT/IL2018/050384, filed on Apr. 2, 2018, entitled "THREE DIMENSIONAL ROBOTIC BIOPRINTER", which claims priority to U.S. Provisional Patent Application No. 62/480,455 filed on Apr. 2, 2017, entitled "3D ROBOTIC BIO PRINTER," each of which are incorporated herein by reference in their entirety.

FIELD OF THE INVENTION

The present invention relates to the field of bioprinting, especially performed in vivo using minimally invasive robotic surgical systems.

BACKGROUND

Tissue engineering using three-dimensional bioprinting has been a promising field of research, offering hope for bridging the gap between organ shortage and transplantation needs. Three-dimensional bioprinting allows tissues, or potentially even organs, to be engineered and subsequently implanted into a subject, drastically reducing the waiting time for treatment of the patient. Furthermore, since the tissues can be engineered from a small amount of the subject's tissue (autologous tissue), use of this possibility can avoid rejection of the implant and the need anti-rejection drugs.

A review of the three-dimensional printing of organs in vitro can be found in the article entitled "3D printing based on imaging data: review of medical applications" by Rengier F. et al, published in International Journal of Computer Assisted Radiology Surgery, 2010 July; 5(4):335-41. doi: 10.1007/s11548-010-0476-x. Epub 2010 May 15.

U.S. Pat. No. 7,051,654 for "Ink-Jet Printing of Viable Cells" to Boland et al, describes "a method for forming an array of viable cells" by "ink-jet printing a cellular composition containing cells onto a substrate, wherein at least about 25% of said cells remain viable on said substrate after incubation for 24 hours" in a humanlike environment. However, this prior art only describes bioprinting viable cells onto a substrate, and does not describe printing directly into the body of a subject.

The article entitled "Direct Human Cartilage Repair Using Three-Dimensional Bioprinting Technology" by Xiaofeng Cui et al, published in Tissue Engineering: Part A, Volume 18, Numbers 11 and 12, 2012, states "This 3D thermal inkjet-based bioprinting/photopolymerization method provides the first example of computer-controlled layer-by-layer construction of material with sufficient mechanical stability for cartilage development". This reference describes printing with a modified HP Deskjet 500 printer onto biopaper in vitro, using 50 nozzles in each printhead, and then checking cell viability 24 hours after printing.

In addition to methods of engineering viable cells, methods and systems have been described for engineering autologous and non-autologous tissues and organs in vitro, and subsequently implanting them into the body of a subject. However, such methods require an opening of the same order as the final dimensions of the printed tissue, thereby considerably increasing the trauma to the surrounding healthy tissues.

For example, the article entitled "3D bioprinting and its in vivo applications" by Nhayoung Hong et al, published by the Department of Biomechatronic Engineering, College of Biotechnology and Bioengineering, Sungkyunkwan University, Suwon, South Korea, describes a bone tissue construct that "was cultured in osteogenic medium for a week and implanted subcutaneously in immuno-deficient mice". Furthermore, this article states "There are still some problems to be solved such as cell viability and the vascularization of printed tissues that are to be organized into larger and more versatile tissues or organs . . . . Vascularization of tissue is the major limiting factor for fabricating human-scale tissue, thus in vivo printing is limited to the small size capable (~few mm) of nutrient diffusion that has clinical relevance." The article further states "one of the important disadvantages of encapsulating living cells in biomaterials is that cell-biomaterial suspensions need to be stored for a considerable period of time in the material reservoir; that compromises cell viability and limits their bioactivity. Thus, a more automated way of loading and ejecting the cell-biomaterial suspension is required . . . ."

The currently available methods and systems for bioprinting directly into the body of a subject, generally developed for cartilage repair which avoids such vascularization problems, require a printing head with elements of substantial size, and require an incision of the same order as the printing head. Some prior art systems also require an invasively inserted sensing device, such as an endoscopic camera. Chinese Patent Application CN 104688388 A for "3D (three-dimensional) printing technique-based cartilage repair system and method" shows, in FIGS. 1 and 2, 3D scanners 5 and a camera 6 located on the nozzle lever 2, both increasing the diameter of the nozzle lever, in addition to a turbocharger 22 that actually juts out from the nozzle lever and further increases the size of the insertable portion of the device. A further disadvantage of this system is that the nozzle lever is rotated by means of a mechanical radial rotating mechanism 4 completely disposed within the anatomical knee cavity. This would appear to substantially increase trauma to the subject's tissues, and to decrease the volume that can be printed upon by the nozzle, possibly requiring multiple insertions to reach the desired volume.

Chinese Patent Application CN 204092271 discloses a pipe for bioprinting within a subject. This reference shows, in FIG. 2, a first pipe body 10 comprising a printing pipe 20, a detection pipe 30 and lighting device 40, all of which increase the diameter of the first pipe body 10. FIG. 1 of this reference shows the image data output port 302 at the distal end of the pipe, increasing the size at the distal end. The device further requires a guide wire for positioning the device properly within the body. Since the device is a flexible pipe, the movement of the pipe is complex and requires imaging elements for real time position analysis. Such complex movements may also increase trauma to the tissue.

In the article entitled "In situ handheld three-dimensional bioprinting for cartilage regeneration" by Di Bella C. et al, published in the Journal of Tissue Engineering for Regenerative Medicine, 2017 May 17, there is described a "handheld 3D printing device (biopen) that allows the simultaneous coaxial extrusion of bioscaffold and cultured cells directly into the cartilage defect in vivo in a single-session surgery". However, the biopen is handheld, such that the accuracy of its positioning is dependent on the surgeon's dexterity. This disadvantage is especially pronounced in cases where the required trajectory to build a three-dimensional biological object is complex. Additionally, if the trajectory of the biopen during the procedure is dependent on the discretion of the surgeon, the surgeon may choose an inefficient path or one resulting in poor outcomes.

Another paramount disadvantage of most contemporary biopens is that such devices are often large to the extent that require a large opening in the subject, even necessitating opening up of the knee joint, for example. This is due to the fact that if more than one type of tissue is to be printed, the biopen requires at least two cartridges, chambers, or compartments hosting different bioink types, and when these cartridges are located within the insertable portion of the biopen, this increases the diameter of the device. For example, the article entitled "Development of the Biopen: a handheld device for surgical printing of adipose stem cells at a chondral wound site" by Cathal D O'Connell et al, published in the Journal Biofabrication, Vol. 8 on Mar. 22, 2016, states "The biopen is composed of a 3D printed chassis housing two ink chambers (labelled 'left' and 'right'), a 3D printed (titanium) extruder nozzle and a UV source. The user (i.e. the surgeon) can control extrusion through each ink chamber individually via a pneumatic extrusion system. Using foot pedals, the surgeon can extrude from the 'left' or the 'right' chamber or both chambers simultaneously." In this reference, not only is the positioning of the biopen dependent on the surgeon's dexterity, but also the extrusion is manually controlled and thus may be dependent on the surgeon's pedicular dexterity. Moreover, when different tissues are to be printed in different layers such as is the case in, for instance, cartilage structures, a handheld device is not able to provide the required thin layers stack, due to lack of accuracy of manually applied layers.

A need therefore exists for systems and methods capable of accurately performing minimally invasive surgeries with a small diameter insertable device, that overcome at least some of the disadvantages of the systems and devices shown in the prior art.

The disclosures of each of the publications mentioned in this section and in other sections of the specification, are hereby incorporated by reference, each in its entirety.

SUMMARY

The present disclosure describes new minimally invasive systems and methods of using surgical robots as three-dimensional printers for fabrication of biological tissues in vivo inside the body of a subject, for example, for cartilage repair. These systems make use of a comprehensive pre-operative plan to accurately direct and control both the motion of the robot during the surgical procedure and the ink extrusion. The two robotic functions are performed in co-ordination with each other. Such systems have a small diameter bio-ink ejecting mechanism, generally in the form of a cannula, and the robotic control is programmed such that angular motion applied to this cannula takes place around a point of rotation at the point of insertion into the subject, in order to minimize trauma to the tissues and to increase the printable volume, thus reducing the need for additional incisions.

The bio-ink ejecting mechanism generally comprises a cannula configured to penetrate a subject, a bio-ink storage volume adapted to host, in predetermined amounts, one or more bio-inks, a bio-ink extruding mechanism, such as a robotically controlled piston, configured to move the one or more bio-inks distally, and a nozzle at the distal end of the cannula adapted to eject the bio-ink inside a subject to form at least one layer of biomaterial. Fabricating the printed tissue inside the body provides the best environment and best incubator for cultivating the printed tissue cells, as opposed to cultivating the tissue in an incubator outside of the body.

Unlike some prior art systems which require multiple bio-ink chambers, that increase the size of the insertable portion of the device, the presently disclosed systems may optionally have only a single, small diameter volume for housing one or more types of bio-ink prior to extrusion. Such a volume may be the cylindrical volume within the cannula, which may be, for example, a needle or catheter. Since the single, small diameter volume may be capable of hosting more than one different bio-ink types, arranged in layers along the length of the storage volume for sequential extrusion, the diameter of the insertable portion of the device may be limited only by the size of the nozzle that should be adequately large to provide sufficient quantity and breadth of ink extrusion. Alternatively, several supply tubes can be connected to a single print head, each with different cell types, similar to some arrangements used in color printer heads.

Furthermore, unlike some prior art systems in which both positioning of the device and bio-ink extrusion are manually controlled, in the presently described systems, both of these can be conveniently robotically controlled, increasing accuracy. A surgical plan may be determined preoperatively that comprises at least one of a predetermined (i) shape, (ii) composition, (iii) position and (iv) size of the three-dimensional tissue element. Since the preoperative plan is comprehensive, it is known in advance which bio-inks will be needed and in which order and amounts. Therefore, the different biomaterials, advantageously provided in gel forms, can be prepared preoperatively in pre-calculated layers in the storage volume of the cannula, in the correct order and amounts according to the surgical plan, thus requiring only a single extrusion device volume and thus decreasing the diameter of the inserted device. This approach considerably reduces trauma to healthy tissues surrounding the target 3D printing area.

The surgical plan may be input to a controller that analyzes the required 3D printable volume, and determines the corresponding required motions of the bio-ink ejecting mechanism during the procedure, in multiple degrees of freedom. The motions of the robot should be directed by the controller such that the cannula of the bio-ink ejecting mechanism follows a predetermined trajectory. The controller may also use analysis of the surgical plan to determine the types of ink required for ejection from the nozzle, and the order, quantities and rates of ejection of these bio-inks.

In addition to directing the surgical robot to manipulate the position and orientation of the bio-extruding mechanism at the surgical site, and to coordinately control ejection of the bio-ink in accordance with a pre-operative surgical plan to form a three-dimensional tissue element, the controller may be further configured to provide requirements for filling the cannula with one or more bio-inks prior to the procedure, in accordance with the pre-operative surgical plan. The requirements should include the amount and types of bio-inks required, and if only a single cylindrical volume is provided, the order and volumes of the required bio-ink layers in the cylindrical volume ink delivery system. The controller executes instructions and processing steps by means of hardware components such as a computer or a microprocessor. The controller may further comprise memory components for storing information.

Some prior art systems require invasively inserted imaging devices in order to enable the surgeon to see the position and progress of the printing procedure, thus contributing disadvantageously to the diameter of the insertable part of the device. In contrast to such systems, a registration process may be used to match the spatial coordinates of the preoperative plan to the coordinate system of the robot and that of the region of the subject into which the bio-ink is being printed during intraoperative 3D fabrication. This obviates the need for an endoscopic camera or any other imaging device on the bio-ink ejecting mechanism itself, which is configured to be inserted into the subject. The registration process may be performed by matching pre-operative images to intra-operative images, or alternatively, by using a navigation tracking system to perform real time tracking of fiducial features and of the robot. By the use of such a registration procedure, the robotic bio-printing system can operate without the need for any imaging, sensing or lighting elements, such that the diameter of the insertable portion of the device can be limited to the required cannula diameter and nozzle opening size for providing adequate flow of bio-ink, whether the cannula is merely a flow cannula with the storage of the bio-ink being positioned proximal of the cannula, or a composite cannula also containing the bio-ink storage volume.

A further feature of the presently disclosed systems is that motion of the nozzle in multi-angled degrees of freedom may be advantageously performed around a single pivot point or fulcrum located at the point of insertion of the device into the subject. The terms fulcrum and pivot point may be used equivalently throughout this disclosure. In addition to any relevant angular positioning around this point of insertion, the cannula may also be moved longitudinally through this point of insertion. This increases the printable volume while reducing trauma to tissues of the subject. Since the bio-ink ejecting mechanism may contain a plurality of bio-ink types, the multi-DOF bio-ink ejecting mechanism may extrude multiple materials in the same horizontal plane, and/or different materials in different horizontal planes. For example, the printing of an intervertebral disc, which consists of annulus fibrosis at the circumference and nucleus pulposus at the center, may be possible by alternating the types of printed bio-ink according to the nozzle-equipped robot position so that the two different materials are deposited at the correct locations, generating the annulus and the nucleus of the intervertebral disc.

In the above described systems and methods, the term three dimensional bioprinting has been used to describe the process for laying down the layers which will generate the in vivo element. This process can take a number of different forms, including both a true ink-jet type of mechanism, in which tiny drops of the bio-ink are ejected either by thermal heating of the bio-ink at the head or by the application of a high intensity acoustic field, either of which generates tiny bubbles, forcing out an equivalent volume of the bio-ink, and an extrusion type of printing head utilizing a syringe with a piston or applied pneumatic pressure, which forces drops of the bio-ink out of a tiny nozzle. Other types of micro-printing are also available. It is to be understood that throughout this disclosure, and as claimed, the term three-dimensional printing, ink jet printing, ink jet extrusion or ejection, and similar terms, are intended to include any such methods of three-dimensional generation of elements by laying down of successive layers, regardless of the particular type of three-dimensional printing head used.

There is thus provided in accordance with an exemplary implementation of the devices described in this disclosure, a system for forming a three dimensional tissue element within a subject, according to a preoperative surgical plan based on at least a three-dimensional preoperative image set, the system comprising:
(i) a cannula configured for insertion into the subject through a surface opening having lateral dimensions of the same order as those of the cannula, the cannula configured to be attached to a surgical robot and comprising a nozzle at its distal end adapted to eject one or more bio-inks to form at least one layer of biomaterial within the subject,
(ii) at least one bio-ink extruding mechanism configured to eject the one or more bio-inks distally from the cannula, and
(iii) a controller adapted:
(i) to direct the surgical robot to adjust the longitudinal position and the orientation of the cannula within the subject in accordance with the preoperative surgical plan, and
(ii) to control the extruding mechanism such that the bio-ink is ejected in accordance with the longitudinal position and the orientation of the cannula within the subject, wherein the system enables forming within the subject of a three-dimensional tissue element having dimensions larger than the lateral dimensions of the cannula, and wherein the surgical robot is configured to perform the adjustments of the orientation of the cannula within the subject, using the surface opening as a pivot point for the orientation of the cannula.

In such a system, the controller may be further adapted to obtain registration of the coordinate system of the surgical robot to the three-dimensional preoperative image set. In the case of either of these systems, the preoperative surgical plan may comprise at least the (i) geometrical form, (ii) composition, (iii) position, and (iv) dimensions of the three-dimensional tissue element.

According to further implementations of such systems, the preoperative surgical plan may be determined, at least in part, by the controller using at least one of (i) image processing of the three dimensional preoperative image set, and (ii) inputs from a surgeon. In such a system, the determination of the preoperative surgical plan my further utilize analysis of data from a medical database.

Yet other implementations may involve a system as described above, in which the one or more bio-inks are housed either (i) in the cannula or (ii) in one or more bio-ink storage volumes fluidly connected to the cannula. According to option (i) of such a system, the cannula may be configured to house at least two bio-inks in layers arranged along the length of the cannula, the layers having predetermined amounts, compositions, and order. In that case, the predetermined amounts, compositions, and order of the layers may be determined by the controller in accordance with the preoperative surgical plan.

According to yet further implementations of such systems, the entirety of the three-dimensional tissue element may be formed without requiring removal of the cannula from the subject. Such a three dimensional tissue element may be formed by (a) performing adjustments of the orientation of the cannula at a first depth in conjunction with incremental longitudinal movements of the cannula, to form a first layer of biomaterial, and (b) subsequently moving the cannula to a second depth within the subject, and performing adjustments of the orientation of the cannula at the second depth in conjunction with incremental longitudinal movements of the cannula to form a second layer of biomaterial, and repeating (b) until the three-dimensional tissue element is formed.

In any of the above described systems, the surface opening can be utilized to provide access to the knee joint of the subject. Additionally, the bio-ink extruding mechanism may be any of a piston, an external pressure application device, a gas pressure device or a bio-ink jet printing head. Furthermore, the diameter of the cannula may be less than 3 mm, or even less than 3 mm.

According to yet further implementations of the above described systems, at least one of the layers of biomaterial may comprise cartilage, bone medium, muscle, blood vessel, or ligament material.

Yet other implementations of such systems may further comprise at least one three-dimensional tracking target associated with the surgical robot, and wherein the controller is adapted to register the coordinate system of the surgical robot to the three-dimensional preoperative image set using the at least one three-dimensional tracking target. In such a case, the system should further comprise reference markers disposed on at least one anatomical element of the subject or fluoroscopically imaged anatomical elements, and wherein the controller is further adapted to use the at least one three-dimensional tracking target to register the coordinate system of the surgical robot to the reference markers or to the fluoroscopically imaged anatomical elements. In such a case, the controller may be further adapted to create a pseudo three-dimensional image comprising the coordinate system of the surgical robot relative either to the anatomical reference markers or to the fluoroscopically imaged anatomical elements, and to correlate a selected window of the pseudo three-dimensional image to a similarly chosen window of the three-dimensional pre-operative image set, such that the position of the surgical robot may be registered with the preoperative surgical plan.

Any of the above described systems may further comprise a steering mechanism for steering the nozzle of the cannula in a desired direction. Furthermore, the cannula may comprise at least one controlled link or joint, such that the nozzle has increased accessibility.

There is further provided in accordance with a further implementation of the present disclosure, a method of determining an operative plan for a surgical robot, A method of determining an operative plan for a surgical robot, the surgical robot utilizing a cannula inserted by the surgical robot into the subject through a surface opening, the cannula comprising at least one nozzle at its distal end adapted to eject one or more bio-inks to form at least one layer of biomaterial within the subject, the method comprising:
 (i) obtaining a three-dimensional preoperative image set of the subject,
 (ii) based on at least the three-dimensional preoperative image set, determining a preoperative surgical plan comprising at least the (a) shape, (b composition, (c) position, and (d) dimensions of a three-dimensional tissue element to be formed by the surgical robot,
 (iii) calculating a planned trajectory for the at least one nozzle in accordance with the preoperative surgical plan,
 (iv) generating a plan for ejection of the one or more bio-inks as the at least one nozzle traverses the planned trajectory, for forming the at least one layer of biomaterial within the subject in accordance with the preoperative surgical plan, and
 (v) inputting the planned trajectory into a controller adapted to manipulate the surgical robot and to control ejection of the one or more bio-inks, such that the nozzle can traverse the planned trajectory in coordination with the plan for ejection, enabling the three-dimensional tissue element to be formed autonomously within the subject, by the surgical robot.

Such a method may further comprise the step of determining planned motion of the surgical robot in accordance with the planned trajectory. Additionally, this planned motion of the surgical robot may be such that any angular motion of the cannula required for the nozzle to traverse the trajectory is performed using a surface opening of the subject as a pivot point. Additionally, in any of the above mentioned methods, the viscosity of the one or more bio-inks may be such that the at least two bio-inks may be disposed in longitudinally arranged layers within the cannula without mixing of the at least two bio-inks.

According to a further implementation of the above described methods, the determining a preoperative surgical plan may comprise accessing a medical database comprising three-dimensional image sets of a plurality of subjects. In such a case, the determining a preoperative surgical plan may be performed by analyzing data from the medical database to determine a surgical plan with the highest statistical likelihood of a positive outcome. Additionally, in any of these methods, at least one of the planned trajectory and the plan for ejection may be calculated using artificial intelligence.

Furthermore, the planned trajectory may be calculated by taking into consideration at least one of (a) avoidance of forbidden regions that would be likely to be damaged by the cannula, (b) the shortest trajectory to form the three dimensional tissue element, and (c) the trajectory that would cause the least trauma to healthy tissues of the subject.

There is further provided in accordance with yet other aspects of the present disclosure, a method of configuring a surgical robot system to form a three dimensional tissue element within a subject, the surgical robot system utilizing a cannula inserted through a surface opening, the cannula configured to eject at least two bio-inks through a nozzle within the subject, the method comprising:
 (i) obtaining a three-dimensional preoperative image set of the subject,
 (ii) determining from the three-dimensional preoperative image set, a surgical plan comprising at least the (a) shape, (b) composition, (c) position, and (d) dimensions of the three-dimensional tissue element,
 (iii) determining a planned trajectory for the nozzle in accordance with the surgical plan, and
 (iv) providing a plan for ejection of the at least two bio-inks as the nozzle traverses the planned trajectory, in accordance with the surgical plan,
  wherein the at least two bio-inks are layered prior to ejection, the amount, position and composition of each layer of bio-ink being selected in accordance with the planned trajectory and with the plan for ejection, such that the three-dimensional tissue element may be formed autonomously by the surgical robot.

In such a method, the layers of the at least two bio-inks may be housed longitudinally along the length of the cannula, and these layers may have predetermined amounts, compositions, and order. Alternatively, in such a method, the layers of the at least two bio-inks may be housed longitudinally in a storage volume fluidly connected to the cannula. Also in the latter case, the layers may be arranged longitudinally along the length of the storage volume and have predetermined amounts, compositions, and order.

Finally, there is further provided a method of performing a hand directed procedure for the generation of a three dimensional tissue element in a subject, comprising,
(i) providing a cannula comprising at least one nozzle at its distal end adapted to eject one or more bio-inks to form at least one layer of biomaterial within the subject,
(ii) inserting the cannula into the subject through a surface opening, and
(iii) manipulating the cannula such that the nozzle follows a trajectory appropriate to generate the at least one layer of biomaterial within the subject, and ejecting the one or more bio-inks in coordination with motion of the nozzle,
wherein the manipulating is performed using an externally disposed imaging system to verify at least that the nozzle is following the trajectory appropriate to generate the at least one layer of biomaterial.

BRIEF DESCRIPTION OF THE DRAWINGS

The present invention will be understood and appreciated more fully from the following detailed description, taken in conjunction with the drawings in which:

FIGS. 3A to 3D are schematic drawings showing exemplary motion patterns of the robotically controlled cannula in accordance with FIG. 1 inserted laterally, using the insertion point of a subject as a fulcrum, to form layers of bio-ink;

FIGS. 4A to 4D, are schematic drawings showing exemplary motion patterns of the robotically controlled cannula in accordance with FIG. 1 inserted vertically, using the insertion point of a subject as a fulcrum, to form layers of bio-ink;

FIG. 6A shows a simple configuration, while FIG. 6B shows a more complex configuration;

DETAILED DESCRIPTION

Figure 1:
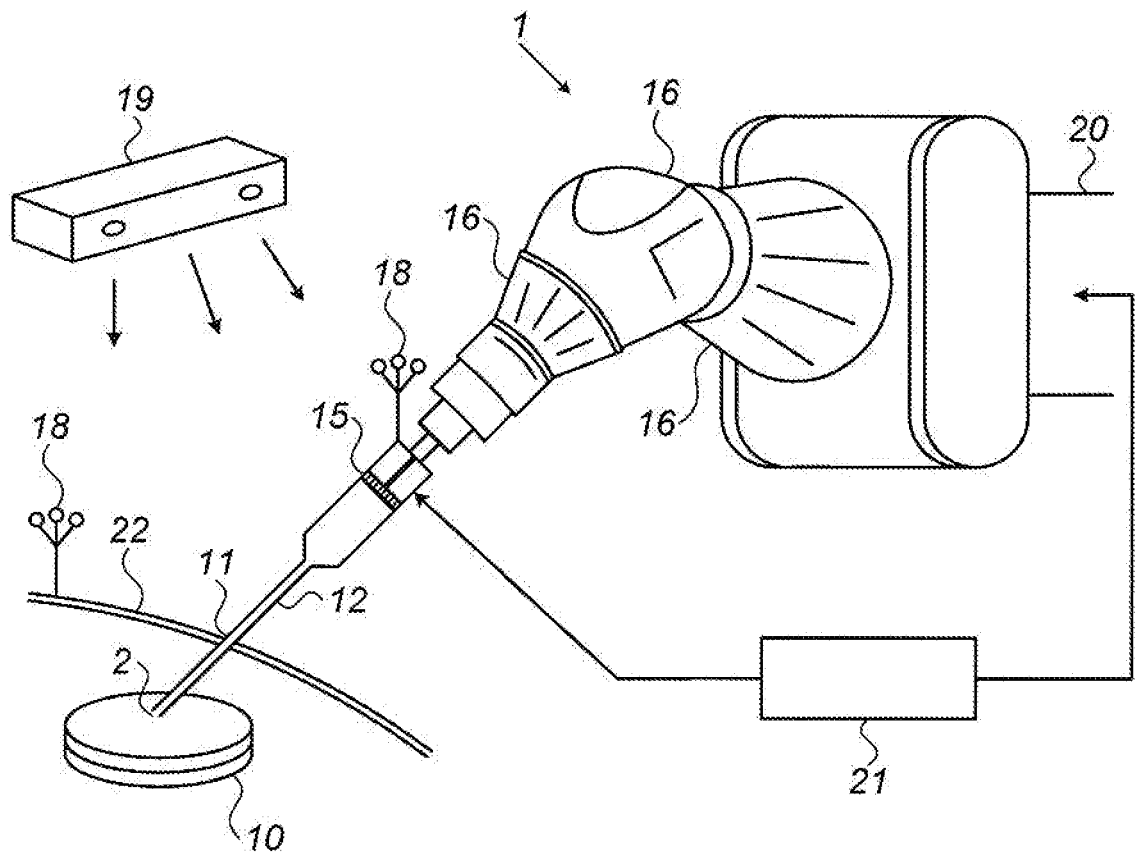
FIG. 1 shows an exemplary schematic robotic surgical system for three-dimensional bio-printing within a subject.

Reference is first made to FIG. 1, showing an exemplary schematic surgical system for robotic 3D bio-printing within a subject. The system comprises a surgical robot 1 configured for 3D in vivo bio-printing, and a controller 21 which is configured both to direct the pose of the surgical robot and also to control the ejection of bio-ink in accordance with the pose of the robot, such as to form a three-dimensional tissue element 10 within the subject. The robotic system may operate autonomously in accordance with a pre-operative surgical plan. The surgical robot is mounted on a base 20, and is adapted to grip in its end effector, an assembly for robotically controlled bio-ink ejection.

The bio-ink ejection assembly comprises a small diameter cannula 12 adapted for minimally invasive insertion into a subject. In FIG. 1, the cannula is shown inserted through an incision 11 in the skin 22 of the subject. The cannula may be equipped with a piston 15 for ejecting one or more layers of bio-ink through the cannula, out of the nozzle 2 at the distal end of the cannula, and into the tissue of the subject. Although the nozzle 2 of the cannula is shown simply as an aperture at the distal end of the cannula, according to other implementations, it can be provided in the form of a hinged nozzle, which can be directed over a range of angles, providing ink ejection in a number of directions without the need to move the cannula. Although piston ejection is shown in the implementation shown in FIG. 1, it is to be understood that alternative robotically controlled bio-ink extruding mechanisms may be utilized, such as a pressure application device located externally to the cannula, a device that exudes gas pressure, mechanical squeezing of a flexible walled bio-ink storage volume, a thermal or acoustically driven ink-jet head, or any other mechanism that is capable of extruding the required amount of bio-ink in an accurate and controlled manner.

In FIG. 1, the cannula is shown having a fine needle section for ejecting the bio-ink into the patient's tissues, and a larger diameter barrel for holding the bio-inks to be injected into the tissue. However, alternative implementations can be used in which the bio-ink syringe cylinder is sufficiently narrow that the whole cylinder can be inserted into the patient's tissue. The bio-ink extruding mechanism is configured to move one or more bio-inks distally towards the nozzle at the distal end of the cannula, which is adapted to control ejection of the bio-ink to form one or more layers of biomaterial. The extruding mechanism should be robotically controlled, such that flow rate and/or amount of extrusion may be accurately metered and directed in accordance with the pre-operative surgical plan and the consequent motion of the nozzle. Alternative cannula implementations having separate bio-ink chambers each containing different bio-ink compositions, may require more than one bio-ink extruding mechanism such that the different types of bio-inks may be extruded separately, as will be shown in FIG. 2B hereinbelow. The cannula may be removable from the surgical robot for ease of sterilization, or may be disposable.

The robot preferably has at least five degrees of freedom, such that it can position the axis of the cannula in space and can also move it along its longitudinal direction. Six or more degrees of freedom can perform the task, generally with simpler robotic programming routines, and the robot's work volume must be able to cover the required treated area. A robot with less than five degrees of freedom may be used, but then also requires use of an additional mechanism that maintains the insertion point fixed in space. The surgical robot shown in the example system of FIG. 1 has a robotic arm for manipulating the cannula 12, having three rotary joints 16.

Whichever robotic configuration is used, it should provide sufficient motion flexibility to the end effector, such that angular motion of the cannula can be performed with the insertion point 11 maintained as a fulcrum or pivot point. Motion of the cannula around a pivot point at the insertion puncture has the advantage of enabling the robot to orientate the cannula at any desired angle with respect to the skin surface of the subject 22, without requiring the initial opening at the insertion point 11 to be larger than that dictated by the diameter of the cannula, and without stressing or even causing trauma at the insertion point 11, or increasing its size during the procedure. Such an arrangement allows for a maximal three-dimensional printing volume to be covered by the cannula through a single, minimally invasive incision.

The surgical robot may thus be manipulated to deposit biomaterials not only in a clearly accessible tissue location, but even within crevices or beneath overhangs in native tissue. The surgical robot may further include a deployable distraction device for distracting tissue that obtrudes the desired location of the printable volume, such a distraction device being sufficiently small that when the device is not deployed, as during insertion, it does not significantly increase the diameter of the cannula. As an alternative, a conventional distraction device may be inserted into the region in which the bio-printing is being performed, through an additional minimally invasive incision at a location different to that through which the bio-printing cannula has been inserted. This arrangement may be particularly useful in tight orthopedic situations, and may provide more flexibility than attempting to distract the bone structures through the same incision through which the bio-printing is being performed. To provide further maneuverability and access within the body, the cannula, or the nozzle of the cannula, can be equipped with a steering device, such as tensioned wire actuators connected to circumferential positions at the nozzle of the cannula, such that the printing head can be steered in order to get into difficult-to-access locations in the body. The steering device can also be robotically controlled and the insertion performed according to the surgical plan. Alternatively or additionally, the steering device can be used in order to change the direction in which the printing nozzle is directed, relative to the axis of the cannula, such that greater flexibility can be obtained over the region in which the printing is performed. Additionally, links and joints can be incorporated into the cannula, to enable it to negotiate complex passages or access paths. The robot can also be programmed to first prepare the region for printing by extracting tissues and bone for instance, as is usually done in endoscopic procedures of the knee joint.

Although the surgical robot is shown here in serial form, the surgical robot may be parallel or hybrid. The surgical robot may be located on a floor, ceiling, bed, or attached to an anatomical feature on which, or near to which, the 3D bio-printing is being performed. The surgical robot may further comprise actuators, additional arms, hinges, and joints, as is known in the art.

Some prior art systems require invasively inserted imaging devices in order to enable the surgeon to see the position and progress of the printing procedure, thus contributing disadvantageously to the diameter of the insertable part of the device. In contrast to such systems, a registration process may be used to match the spatial coordinates of the pre-operative plan to the coordinate system of the robot and that of the region of the subject into which the bio-ink is being printed during intraoperative 3D fabrication. This obviates the need for an endoscopic camera or any other imaging device on the bio-ink ejecting mechanism itself, which is configured to be inserted into the subject. The registration process may be performed by matching pre-operative images to intra-operative images, or alternatively, by using a navigation tracking system to perform real time tracking of fiducial features and of the robot. By the use of such a registration procedure, the robotic bio-printing system can operate without the need for any imaging, sensing or lighting elements, such that the diameter of the insertable portion of the device can be limited to the required cannula diameter and nozzle opening size for providing adequate flow of bio-ink, whether the cannula is merely a flow cannula with the storage of the bio-ink being positioned proximal of the cannula, or a composite cannula also containing the bio-ink storage volume. However, it is to be understood that real time imaging performed externally to the subject, such as X-ray, CT or ultrasound, can be used to verify the position of, or even to guide the robotic probe in real time, without the need to insert any additional invasive imaging elements into the subject. This latter application, namely the provision of a real-time imaging device, such as a C-arm fluoroscopic system or an alternative imaging method, enables the achievement of higher accuracy hand-held bio-printing to be performed. The use of such an imaging device provides real-time information on the printing position and progress, without the need of an imaging device such as endoscopic camera, inserted into the subject's body, thereby increasing the size of the cannula, as already mentioned hereinabove. The imaging device can be positioned such that it images the region in which the three-dimensional bio printed element is being formed, and should preferably be aligner ball such that it can image the printing progress from a number of alternative angles.

As previously mentioned, the present system uses a registration process in order to match the spatial coordinates of the preoperative plan to the coordinate system of the robot and the region of the subject which the bio ink is being printed. One method of doing this is by the matching of preoperative three-dimensional images to intraoperative fluoroscope images of the region being printed. This can be advantageously performed by matching of anatomical features of the imaged region, with an indication of the robot position, and hence its coordinates, shown in both sets of images. The robot position can alternatively be related to the region being bio-printed, by the use of a navigation tracking system performing real time tracking of the robot and of fiducial features, such as tracking elements mounted on the anatomy of the patient. These fiducial features should also be present in the preoperative three-dimensional images. In the exemplary system shown in FIG. 1, such a tracking system is being utilized, as illustrated by the tracking camera 19 mounted over the region in which the operation is being performed, and reference markers 18 mounted on an anatomical feature of the subject, and on a spatially defined component of the robot or of the bio ink injection mechanism, such as the cannula. Use of such reference markers on the subject and on the robot obviate the need for providing a fixed relationship between the robot position and the subject's position.

Figure 2A:
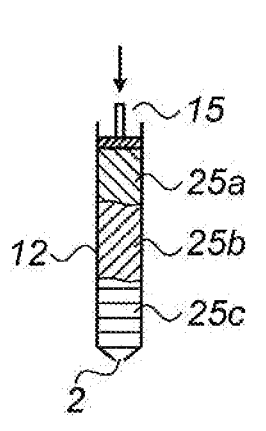
FIGS. 2A and 2B show exemplary alternative bio-ink ejection mechanisms of the surgical system of FIG. 1.
Figure 2B:
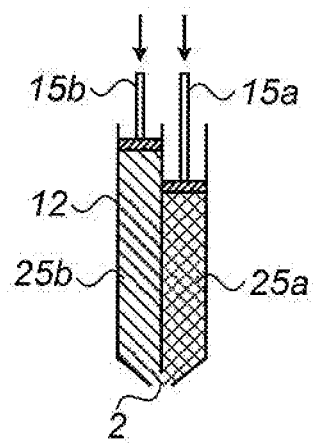

Reference is now made to FIGS. 2A and 2B, which show exemplary alternative bio-ink ejection mechanisms of the surgical system of FIG. 1. FIG. 2A shows an exemplary bio-ink ejecting mechanism having a cylindrically shaped cannula 12 configured to penetrate a subject, and a robotically controlled piston 15. Although in its simplest form, the cannula may contain a single bio-ink which is to be printed, the cannula of FIG. 2A is shown hosting alternate layers of three types of bio-inks having different compositions, bio-ink 25A, bio-ink 25B and bio-ink 25C, but it is to be understood that either a single type of bio-ink or any other number of bio-inks may be layered in amounts and combination in accordance with the surgical plan. The bio-ink layers may be stacked longitudinally (i.e. along the length of the cannula) within the cannula in predetermined amounts, compositions, and order, in accordance with the surgical plan. The required bio-ink layers may be advantageously determined by using a controller to extrapolate from the surgical plan, a planned motion profile and trajectory and a plan for ejection coordinated with the motion plan and trajectory. The ejection plan could, for example, define the speed of the longitudinal movement of the piston through the cannula. This layered arrangement allows the layers of bio-ink to be extruded sequentially out of nozzle 2 by the piston 15 during the procedure. In order for this implementation to be effective, the bio-inks should preferably be of a viscosity such that they do not mix significantly within the cannula, such as in paste or gel form. The robotic system may further comprise a robotic loading dock (not shown) that pre-operatively fills the cannula with the required bio-ink layers in accordance with the requirements determined by the controller, providing a high level of accuracy in the amount, order and composition of the bio-ink layers, and contributing to the autonomy of the robotic system. Alternatively, the layers within the cannula may be prepared manually.

Reference is now made to FIG. 2B, showing an exemplary alternative bio-ink ejection mechanism of the surgical system of FIG. 1. In this implementation, separate channels are provided within the cannula 12 for different bio-ink types 25A and 25B, with the channels being of small diameter and in close proximity to one another to maintain the desired small diameter cannula. The cannula tapers at the distal end where there is located a single nozzle 2 for in vivo extrusion of bio-ink. In this drawing, two channels are shown, but it is to be understood that any number of channels may be used. Two separate robotically controlled pistons 15A and 15B are provided, such that the different bio-ink types 25A and 25B may be extruded separately.

In alternative implementations, the bio-ink or bio-inks may be hosted partially or completely outside of the cannula, and may be housed in a volume of any shape, but should be fluidly connected to the inner volume of the cannula to provide flow of bio-ink distally through the cannula. The cannula may further comprise a miniature UV light, that does not significantly increase the diameter of the insertable portion of the robot, for polymerization of the bio-inks. It is to be understood that the term "cannula" used throughout this disclosure may be a needle, a catheter, or any other insertable surgical tool.

Reference is now made to FIGS. 3A to 3D, which are schematic drawings showing exemplary motion patterns of the robotically controlled cannula 12, having a nozzle 2 at its distal end, in accordance with FIG. 1, using the insertion point 11 of a subject as a fulcrum, to form layers of bio-ink. FIGS. 3A to 3D show an exemplary implementation in which the cannula 12 is inserted into the subject laterally, such as into the knee of the subject for the purpose of injecting a three dimensional cartilage element, as will be shown with more detail in FIG. 4. In FIG. 3A, the cannula 12 is minimally invasively inserted into the subject to the desired depth, through an incision 11 in the skin of the subject 22 that is designated by the surgical plan and/or the planned trajectory determined by the controller or the surgeon. It may be noted that in this optimal implementation of the presently disclosed system, the insertion opening incision 11 is limited only by the size of the cannula 12 itself.

Reference is now made to FIG. 3B, where the angle of the cannula 12 is robotically adjusted by the surgical robot as bio-ink is extruded from the nozzle 2 to form the first layer of bio-ink 30 in vivo within the subject. As mentioned previously, the multiple degrees of freedom provided by the surgical robot allow for the insertion point to be maintained as a fulcrum. It may be seen in this drawing how the cannula 12 is manipulated around the single insertion point 11 without stressing, tearing or expanding the opening. It is possible to print a straight line layer, or indeed any other line shape, by programming the robot to co-ordinate a linear motion of the cannula with its angular motion.

Reference is now made to FIG. 3C, where the cannula 12 is shown being withdrawn longitudinally, to a position at which a second layer 31 of bio-ink is to be formed, adjacent to the first layer 30. The angle of the cannula 12 is robotically swept in the new longitudinal position while bio-ink is controllably ejected, thus forming a second layer of bio-ink 31. Although there is a gap shown in the drawing between the first layer 30 and second layer 31, it is to be understood that each bio-ink layer is generally formed in contact with the previous layer, such that a planar tissue element may be formed 10. The process repeats, with the cannula 12 being withdrawn further and with more layers being formed, until this first lateral layer is complete in accordance with the surgical plan and/or the planned trajectory.

In order to build up a true three-dimensional printed element, it is now necessary to print additional bio-layers on top of the first tissue layer. Reference is now made to FIG. 3D, where it is shown how the cannula 12 is adjusted to proceed to print the next lateral level such that a new layer 32 may be formed within the next lateral level. The process shown in FIGS. 3B and 3C, then is repeated at the new lateral level. Even within a single layer, different types of cells can be used. After all the required lateral levels have been accessed by the cannula, and the required layers have been formed at each lateral level, the three-dimensional tissue element is complete, and the cannula may be withdrawn completely from the subject.

FIGS. 3A to 3D illustrate the formation of layers with the cannula performing motion approximately parallel to the layers being printed. This configuration is useful for the generation of layers in locations with limited headroom. However, it is also possible, and generally simpler where the anatomical geometry allows, to print layers while the cannula executes motion while it is approximately perpendicular to the layer being printed.

Reference is now made to FIGS. 4A to 4D, which are schematic drawings showing such exemplary motion patterns of the robotically controlled cannula 12 inserted vertically in accordance with FIG. 1, using the insertion point 11 in the skin 22 of a subject as a fulcrum, to form layers of bio-ink.

Reference is first made to FIG. 4A, which shows the cannula 12 being inserted generally vertically, through a minimally invasive incision 11 in the skin 22 of a subject towards a target 3D printing area (not shown). The workspace 40, which is the potential volume in which layers of tissue may be formed by the surgical robot, is shown to be cone-shaped, which is the maximal workspace volume possible resulting from a single fulcrum. As in the implementation of FIGS. 3A to 3D, the insertion opening 11 should be limited only by the size of the cannula 12 itself.

Reference is now made to FIG. 4B, which shows the cannula 12 being orientated around the incision 11 as a fulcrum, while bio-ink is ejected from the nozzle 2, to form a first lateral layer of bio-ink 41 within the subject, which is generally the deepest layer. The layer 41 in this drawing is shown to be circular, but may be of any shape, in accordance with the surgical plan and/or the planned trajectory. As mentioned previously, the multiple degrees of freedom of the surgical robot (shown in FIG. 1), allow for the insertion point 11 to be maintained as a fulcrum. It may be seen in this drawing how the cannula 12 is manipulated around the single insertion point 11 without stressing, tearing or expanding the opening 11.

Reference is now made to FIG. 4C, which shows the cannula 12 being robotically withdrawn longitudinally by a predetermined amount through the incision 11, by use of the robotic activation arm, to prepare for a second layer of bio-ink 42 to be formed. The angle of the cannula 12 is robotically adjusted in the new longitudinal position to while bio-ink is controllably ejected from the nozzle 2, thus forming a second layer of bio-ink 42. Although there is a gap shown in the drawing between the first layer 41 and second layer 42, it is to be understood that each bio-ink layer is generally formed in contact with the previous layer, such that a three-dimensional tissue element 10 may be formed. The process repeats, with the cannula 12 being withdrawn incrementally further and with more layers being formed, until the most superficial layer is complete in accordance with the surgical plan and/or the planned trajectory.

Reference is now made to FIG. 4D, showing a completely formed three-dimensional tissue element 10. Since the 3D printing process is complete, the cannula 12 is being withdrawn completely from the subject through the incision 11 in the skin surface 22 in a manner that does not increase the size of the incision 11.

Since the techniques illustrated in FIGS. 3A to 3D and 4A to 4D minimize trauma, in some cases it may be advantageous to perform the procedure in several stages, building a subsequent layer after the previous one has been healed, thereby enhancing the structural rigidity of the printed volume.

Figure 5:
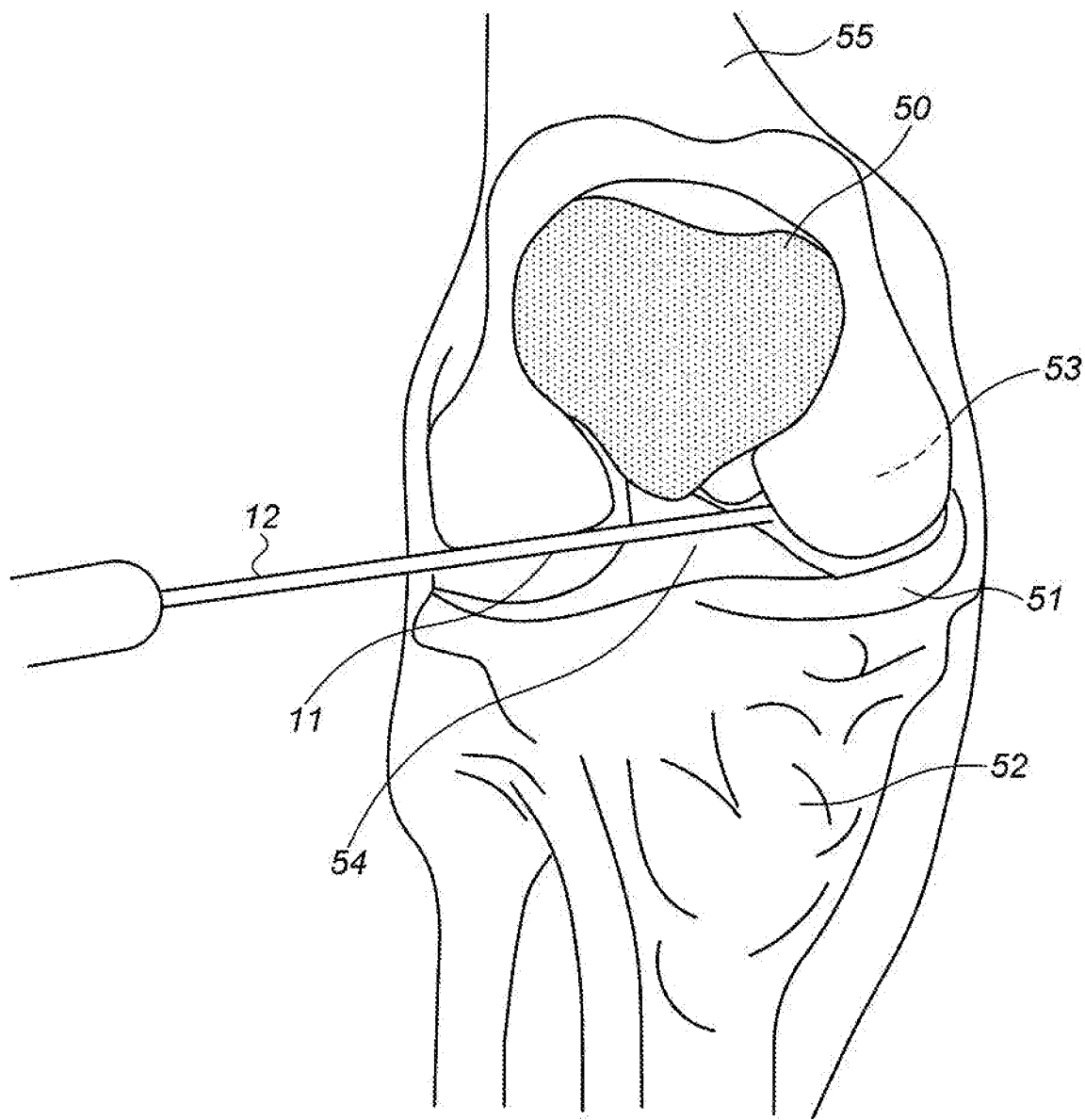
FIG. 5 shows an exemplary application of the presently disclosed robotic surgical system being used to form a three-dimensional cartilage element within the knee of a subject.

Reference is now made to FIG. 5, which shows an exemplary application of the presently disclosed robotic surgical system, being used to form a three-dimensional cartilage element in situ within the knee of a subject, generally reinforcing and augmenting the remaining cartilage in the joint. This application particularly shows the advantage of the present system, since the limited space available would make it very difficult to insert a preformed cartilage element into the knee joint, and its likelihood of being accepted would be less than an element deposited in situ within the joint. The fabrication of knee cartilage is performed through a lateral minimally invasive incision 11, which may be as small as 1 mm. Because of the very limited space available for this application, the cannula 12 uses a fine needle for ejecting the bio-ink to the region to be applied, with the bio-ink or inks being stored for ejection in a syringe-like cylinder proximal to the needle cannula. The needle cannula 12 is shown passing inferior to the patella 50, superior to the medial meniscus 51 and superficial to the anterior cruciate ligament 54, and into the articular cartilage 53 of the knee (the point of application being hidden beneath the medial condyle), where bio-ink will be ejected from the nozzle of the cannula (shown in FIG. 1) to form a three-dimensional cartilage element. The femur 55 and tibia 52 are also shown. The manipulations of the cannula 12 are controlled by the surgical robot 1 in accordance with instructions provided by the controller. Coordinated motion of the robotic joints allow the insertion point 11 to be maintained as the fulcrum of the motion throughout the procedure. Because of the tight space available, this procedure may require the application of an external distraction device.

Figure 6A:
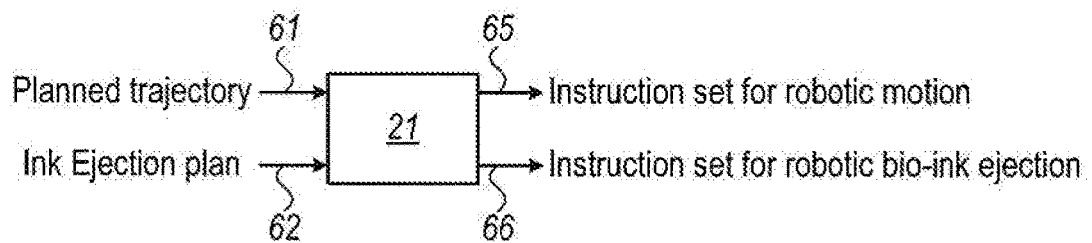
FIGS. 6A and 6B show schematically overviews of exemplary controller configurations of the presently disclosed robotic surgical system, and the inputs and outputs therefrom.
Figure 6B:
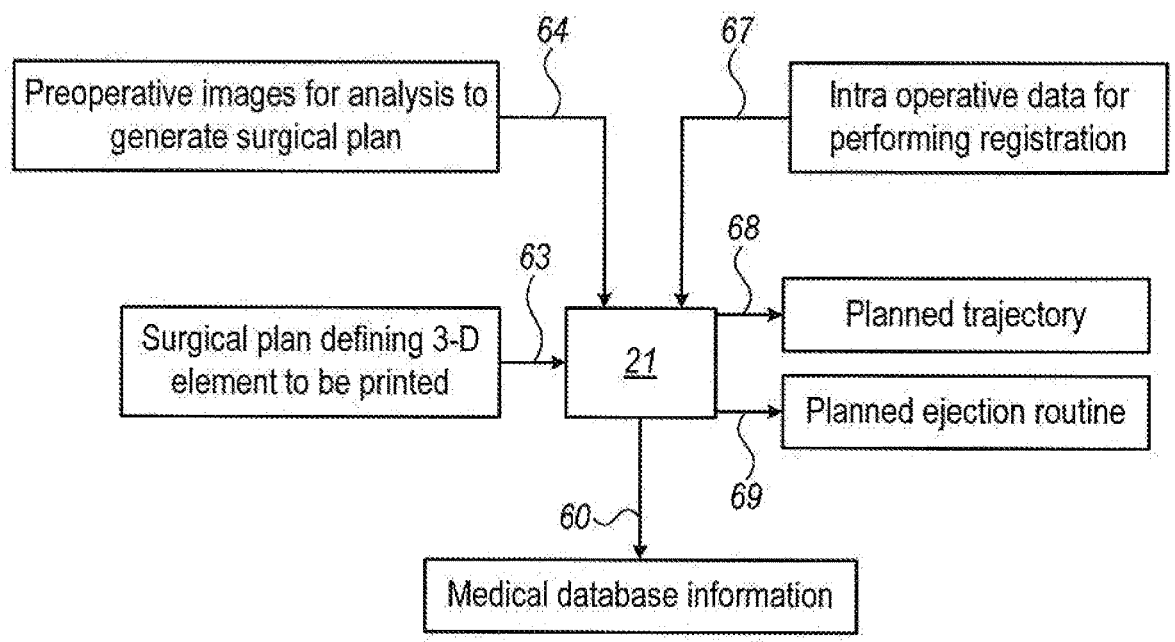

Reference is now made to FIGS. 6A and 6B, which show an overview of exemplary configurations for the processes performed by the controller 21 of the presently disclosed robotic surgical system, and the inputs thereto and the outputs therefrom. FIG. 6A shows a simple configuration for the controller 21, in which the inputs may be a planned cannula nozzle trajectory at input 61, and the ejection routine associated with that trajectory, at input 62. This input information may be determined by the surgeon based on the needs of the subject as diagnosed from the preoperative images. Based on his/her experience, and on an analysis of the preoperative images, the surgeon can plan the shape, size, composition and position of the desired bio-printed element or organ. In this first configuration, the outputs from the controller 21 will be a set of instructions 65 to the robotic system to execute the surgeon's planned trajectory, and an associated set of instructions 66 to the bio-ink robotic ejector mechanism, to execute the plan for bio-ink ejection 66 in coordination with the robotic trajectory of the cannula nozzle, to generate the surgeon's planned printed element.

FIG. 6B shows a second and higher level configuration for the controller 21, in which the inputs may be a surgical plan 63, defining a predetermined shape, composition, position and size of the three-dimensional tissue element to be printed. Alternatively, the preoperative images of the region to be treated may be directly input 64 to the controller, which is configured to perform analysis thereof, to determine an acceptable or optimal surgical plan, which may include use of Artificial Intelligence including accessing a medical database 60, and extracting information therefrom. Such analysis may include, inter alia, analysis of the preoperative images to determine the extent of tissue damage, a diagnosis based on the subject's medical profile, knowledge from a database of similar cases which included the 3D bio-printing procedure performed on this region, and the outcome thereof, and any other clinically relevant factors. The surgical plan may be selected by the controller based on many other factors, such as, for instance, the need to avoid forbidden regions that may be damaged by the cannula, the type or density of tissue at the target site, the shape of anatomical features at the target site, size limitations of the three-dimensional tissue element due to constraining anatomical boundaries, and position or size limitations intended to reduce trauma to the tissues of the subject.

In addition to the input 64 and analysis of preoperative images for determination of a surgical plan, the controller may use such preoperative images of the subject for image registration purposes. Such images may be registered with intraoperatively obtained data, such as that input 67 to the controller from reference markers or fluoroscopically imaged anatomical elements, to allow the controller to determine the intraoperative location of the surgical robot relative to the subject and also relative to the surgical plan obtained from the preoperative images, and accordingly to direct the surgical robot to the appropriate pose.

According to a further proposed aspect of the system implementation, the controller may be configured to compare the subject's preoperative 3D images 64 of the region of interest to those expected from healthy persons having a similar medical profile to that of the subject, as obtained from a database 60, such that the controller may determine the optimum shape, size, and/or position of a volume of tissue needed to be implanted in order to bring the subject's region of interest back to the characteristics of a healthy person. A finite element or voxel analysis may be performed on an equivalent volume in the above mentioned images of healthy persons, and the levels of grayscale units of this volume may be converted to corresponding bio-ink materials that would provide the correct density at each location, to create a bio-ink map that will be a part of the surgical plan. Alternatively or additionally, a shape, volume or position of tissue for the surgical plan may be determined from an analysis of patients with a similar diagnosis or damage, e.g., cartilage damage, and then the plan may be calculated based on the highest statistical likelihood of a positive outcome.

By whatever means the surgical plan is determined, parameters generated from the preoperative planning may be stored in the controller for positioning the robot and for coordinated ejection of the bio-ink during the surgical procedure.

The outputs from the controller 21 shown in FIG. 6B are the planned trajectory 68 and the plan for ejection 69, which are to be performed after processing the surgical plan. The planned trajectory should be the most efficient or optimal trajectory, and may be calculated by taking into consideration at least one of (i) avoidance of forbidden regions that would be likely to be damaged by the cannula, (ii) the shortest trajectory to form the three dimensional tissue element, and (iii) the trajectory that would cause the least trauma to healthy tissues of the subject. The plan for bio-ink ejection may comprise the speed of the bio-ink extrusion mechanism, such as piston motion, the elapsed times for ejection of the bio-inks, and/or metered amounts of bio-inks to be extruded. The planned flow rate and planned trajectory should be determined such that they may operate in conjunction to allow the surgical robot to fulfill the surgical plan autonomously. The controller may also use the planned trajectory and the plan for ejection to determine the predetermined amounts, compositions, and order of layers of bio-ink required for preparing the cannula pre-operatively in accordance with the surgical plan. The controller may select a certain type of bio-ink that is optimal for the procedure, out of a range of possible bio-inks. Additionally, if the surgeon determines otherwise, he/she may override the system's selection and may substitute an alternative bio-ink into the surgical plan for recalculation of the optimum output.

Figure 7:
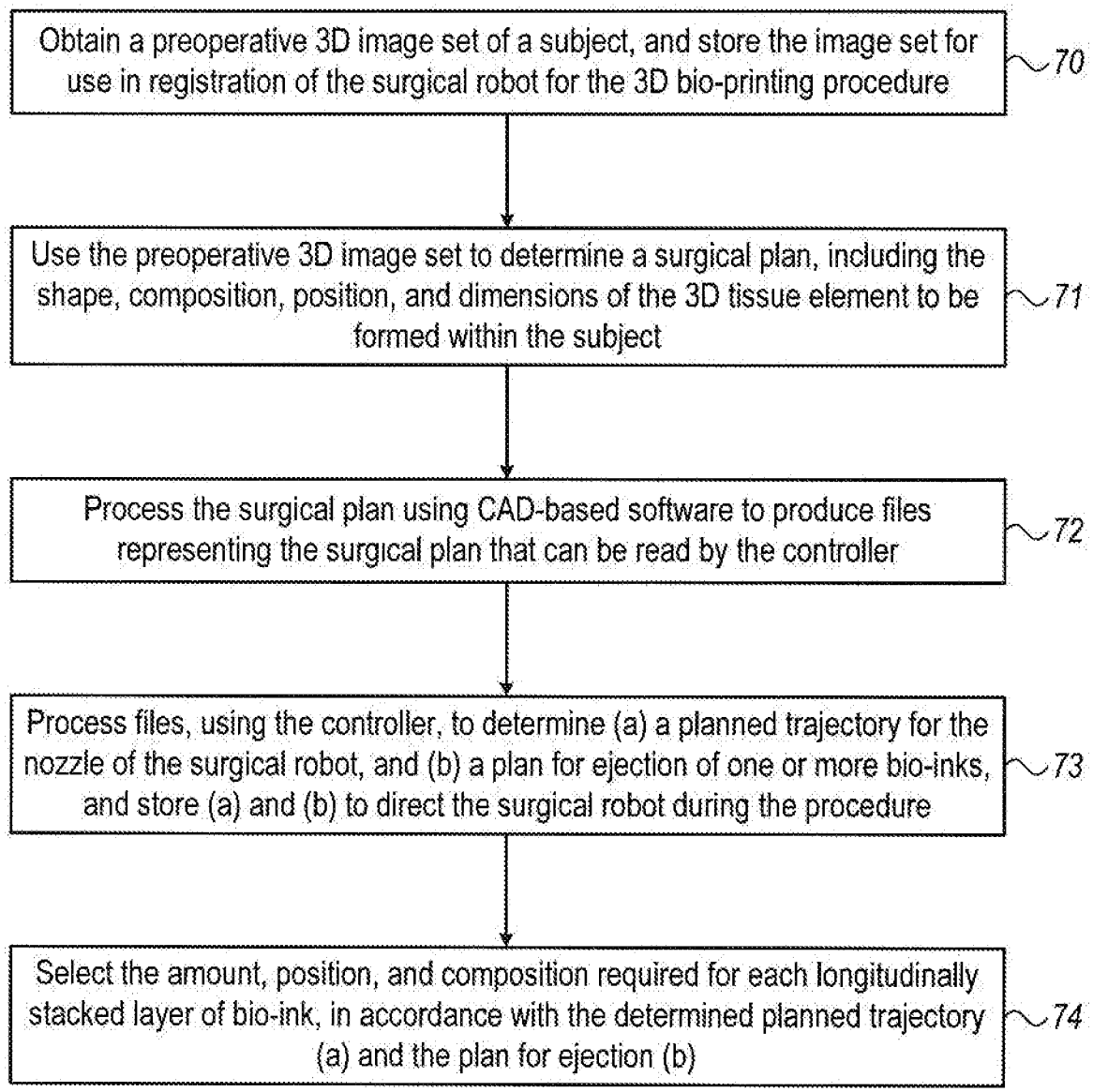
FIG. 7 shows an exemplary method of planning a robotic 3D bio-printing procedure using a controller.

Reference is now made to FIG. 7, which is a flowchart illustrating one exemplary method of planning a robotic three dimensional bio-printing procedure using controller 21. In step 70, a 3-dimensional image set of a subject is obtained, such as derived from MRI, CT or ultrasound images, and the image set is stored for use in registration of the surgical robot for the 3D bio-printing procedure. In step 71, the preoperative 3-dimensional image set is used to determine a surgical plan, including the shape, composition, position, and dimensions of the 3-dimensional tissue element to be formed within the subject. The controller then converts the surgical plan into a set of operational characteristics which include the type, shape and size of the layers to be printed, the correct position of the three-dimensional object relative to the subject's anatomy, and the correct bio-ink component for each location within the shape. As one non-limiting example, a user may electronically position and insert dots representing different types of bio-inks onto a virtual preoperative image to create a desired three-dimensional shape.

In step 72, the surgical plan is processed typically by using CAD-based software to produce files representing the surgical plan that may be read by the controller.

In step 73, the files are processed, using the controller to determine (a) a planned trajectory for the nozzle of the surgical robot, and (b) a plan for ejection of one or more bio-inks, the planned trajectory and plan for ejection being stored to direct the surgical robot and the ejection mechanism during the procedure. The planned trajectory and the plan for ejection may be considered together an operative plan comprising the required robotic printer motion in multiple degrees of freedom to achieve the desired trajectory, and the required locations and types of bio-ink ejection during this motion. It may thus be determined with a high level of accuracy, which motions will be required for the robotic arm of the surgical robot to enable both compliance with the planned trajectory and maintenance of the pivot point. Likewise, the motions or actuations of the extrusion mechanism, such as the precise required speed of the piston required throughout the procedure, may also be determined.

The planned trajectory and plan for ejection may be determined as described hereinabove in accordance with FIG. 6B. Using the example of the method performed with a surgical system having a small diameter cannula with a single cylindrical volume for hosting bio-inks, in step 74, the amount, position, and composition required for each longitudinally stacked layer of bio-ink is determined, in accordance with the determined planned trajectory and plan for ejection. In alternative methods of the present disclosure, such as if only one type or composition of bio-ink is required, or if the cannula is divided into separate chambers adapted to host different bio-ink types, the separate chambers being independently activated, this step 74 may not be necessary.

Figure 8:
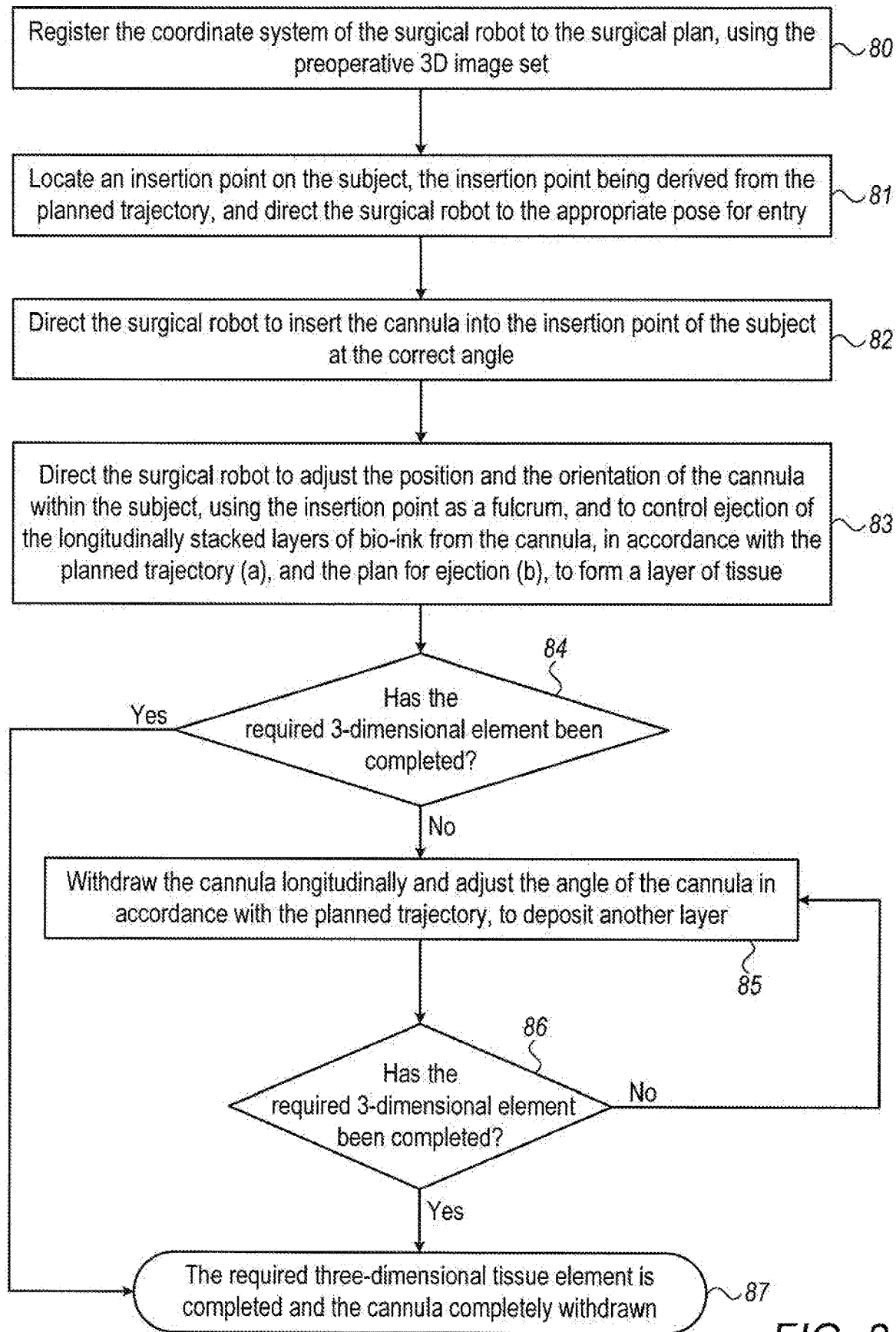
FIG. 8 shows an exemplary method of performing a robotic 3D bio-printing procedure using a controller.

Reference is now made to FIG. 8, which shows an exemplary method describing the practical steps of performing a robotic 3-dimensional bio-printing procedure generated using the controller 21 to also perform the registration of the intraoperatively obtained images with the preoperative plan, and the co-ordinate system of the robot with that of the preoperative images. Although the steps shown in FIG. 8 comprise a comprehensive procedure, it is to be understood that all of the steps are not essentially generated by the controller, but that some may be performed or input by externally decided steps or by a surgeon's intervention.

In step 80, the coordinate system of the surgical robot is registered to the surgical plan, using the preoperative 3D image set. In step 81, an insertion point is located on the subject, the insertion point being derived from the planned trajectory, and the surgical robot is directed to the appropriate pose for entry. In step 82, a minimally invasive surgical incision is made in the subject, and the surgical robot is directed to insert the small diameter cannula at the insertion point of the subject at a predetermined angle, as determined by the surgical plan. Since the print-head does not comprise imaging elements that would increase its size, the procedure may be performed minimally invasively through a small opening, for example 1 mm. This greatly reduces trauma to the surrounding tissues and decreases recovery time for the subject.

In step 83, once the cannula has reached the required entry depth in accordance with the planned trajectory, a first layer of bio-ink is controllably ejected by the extrusion mechanism in coordination with motion of the cannula, as controlled by the surgical robot. As shown previously in FIGS. 3A to 3D and 4A to 4D, the insertion point of the subject should be maintained as a pivot point throughout this process. The first layer of bio-ink is ejected in the correct shape, composition, position relative to the subject, and dimensions, by directing the surgical robot in accordance with the planned trajectory and the plan for ejection.

After a layer of bio-ink has been formed, in step 85, it is determined whether the required 3-dimensional tissue element has been fully generated. If not, the system instructs in step 85 that the cannula be withdrawn longitudinally by a predetermined incremental amount, and the angle of the cannula adjusted in accordance with the planned trajectory to form a second layer of bio-ink. Step 85 is described for the lateral procedure described in FIGS. 3A to 3D. The required motion for performance of the procedure of FIGS. 4A to 4D should be amended accordingly. In step 86, the system then again checks whether the required 3-dimensional tissue element has been fully generated. If not, the system instructs that step 85 be repeated. If the 3-dimensional tissue element has been completed, the procedure may be concluded, as in step 86, and the cannula is withdrawn completely from the subject. If additional incisions are required to fulfill the size and shape requirements of the required three-dimensional object, steps 81 to 87 may be repeated, either during the same procedure or during another procedure at a later date.

The method of FIG. 8 is generally performed autonomously by the controller and the surgical robot; however, the controller may receive optional user inputs such as if the surgeon wishes to interrupt the procedure or override the predetermined surgical plan. A practitioner may alter the planned robotic printer motion, or the locations and types of bio-ink ejection during this motion, if desired. For example, the planned trajectory may be based on an efficiency algorithm and may be a trajectory for a single surgical procedure, but the surgeon may decide to break up the surgical plan into two procedures, building a subsequent layer after the previous one has been healed, thereby enhancing the structural rigidity of the printed volume.

In conclusion, the presently disclosed systems and methods offer a high degree of accuracy, low trauma, small incision size, minimal exposure to radiation, and a lesser chance of infection than may be encountered from an in vitro bio-element printing procedure, followed by insertion of the element by a more drastic surgical procedure.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A system for forming a three-dimensional tissue element, the system comprising:
 a cannula having a proximal portion opposite a distal portion and first lateral dimensions, the cannula configured for insertion into a subject through a surface opening having second lateral dimensions, the proximal portion configured to be attached to a surgical robot and the distal portion comprising a nozzle adapted to eject one or more bio-inks to form at least one layer of biomaterial within a region of the subject;
 at least one bio-ink extruder configured to eject the one or more bio-inks from the distal portion of the cannula; and
 a controller adapted:
  to register a coordinate system of the surgical robot to a three-dimensional preoperative image set including three-dimensional preoperative images of the region of the subject, wherein a preoperative surgical plan for ejecting the one or more bio-inks is determined based on at least the three-dimensional preoperative image set;
  to direct the surgical robot within the registered coordinate system to adjust a longitudinal position of the cannula and, using the surface opening as a pivot point, an orientation of the cannula within the subject in accordance with the preoperative surgical plan; and
  to control the at least one bio-ink extruder such that the one or more bio-inks is ejected in accordance with the longitudinal position and the orientation of the cannula to form, within the subject, a three-dimensional tissue element having dimensions larger than the first lateral dimensions.

2. The system of claim 1, wherein the preoperative surgical plan comprises a plan for a number of layers in the at least one layer of biomaterial, a plan for a type of bio-ink for each layer of biomaterial, and a plan for an order in which the number of layers are formed.

3. The system of claim 1, wherein the preoperative surgical plan comprises at least (i) a geometrical form, (ii) a composition, (iii) a position, and (iv) dimensions of the three-dimensional tissue element.

4. The system of claim 1, wherein the three-dimensional tissue element is entirely formed without requiring removal of the cannula from the subject.

5. The system of claim 1, wherein the three-dimensional tissue element is formed by (a) performing adjustments of the orientation of the cannula at a first depth in conjunction with incremental longitudinal movements of the cannula, to form a first layer of biomaterial, and (b) subsequently moving the cannula to a different depth within the subject and performing adjustments of the orientation of the cannula at the different depth in conjunction with incremental longitudinal movements of the cannula to form another layer of biomaterial, and (c) repeating (b) until the three-dimensional tissue element is formed.

6. The system of claim 1, wherein the surface opening is an opening providing access to a knee joint of the subject.

7. The system of claim 1, wherein at least one the bio-ink extruder is any of a piston, an external pressure application device, a gas pressure device or a bio-ink jet printing head.

8. The system of claim 1, wherein a diameter of the cannula is less than 1 mm.

9. The system of claim 1, wherein a diameter of the cannula is less than 3 mm.

10. The system of claim 1, wherein the at least one layer of biomaterial comprises cartilage, bone medium, muscle, blood vessel, or ligament material.

11. The system of claim 1, further comprising an actuator for steering the nozzle of the cannula in a desired direction.

12. The system of claim 1, wherein the cannula comprises at least one controlled link or joint configured to increase accessibility of the nozzle.

13. The system of claim 1, wherein the first lateral dimensions are similar to the second lateral dimensions.

14. The system of claim 1, wherein the preoperative surgical plan is determined at least in part by the controller using (i) image processing of the three dimensional preoperative image set or (ii) inputs from a surgeon.

15. The system of claim 14, wherein the determination of the preoperative surgical plan further utilizes analysis of data from a medical database that includes images of a volume from another subject that corresponds to the region of the subject, and wherein the analysis includes converting grayscale values within the images of the volume into corresponding bio-ink materials that provide a correct density at each location within the three-dimensional tissue element.

16. The system of claim 1, wherein the one or more bio-inks are housed either (i) in the cannula or (ii) in one or more bio-ink storage volumes fluidly connected to the cannula.

17. The system of claim 16, wherein the one or more bio-inks include at least two bio-inks are housed in the cannula, and wherein the cannula is configured to house the at least two bio-inks in layers arranged along a length of the cannula, the length extending from a proximal end to a distal end of the cannula.

18. The system of claim 17, wherein the controller is adapted to determine an amount of bio-ink for each layer based on the preoperative surgical plan.

19. The system of claim 1, further comprising at least one three-dimensional tracking target associated with the surgical robot,
- wherein the controller is adapted to register the coordinate system of the surgical robot to the three-dimensional preoperative image set using the at least one three-dimensional tracking target.

20. The system of claim 19, further comprising either reference markers disposed on at least one anatomical element of the subject or fluoroscopically imaged anatomical elements,
- wherein the controller is further adapted to use the at least one three-dimensional tracking target to register the coordinate system of the surgical robot to the reference markers or to the fluoroscopically imaged anatomical elements.

21. The system of claim 20, wherein the controller is further adapted to create a pseudo three-dimensional image comprising the coordinate system of the surgical robot relative either to the reference markers or to the fluoroscopically imaged anatomical elements, and to correlate a selected window of the pseudo three-dimensional image to a similarly chosen window of the three-dimensional preoperative image set, such that a position of the surgical robot is registered with the preoperative surgical plan.

22. A system for forming a three-dimensional tissue element, the system comprising:
- a surgical robot comprising a robotic arm with one or more rotary joints and an end effector;
- a cannula having a proximal portion opposite a distal portion and first lateral dimensions, the cannula configured for insertion into a subject through a surface opening having second lateral dimensions, the proximal portion configured to be directly attached to the end effector of the robotic arm and the distal portion comprising a nozzle adapted to eject one or more bio-inks to form at least one layer of biomaterial within a region of the subject;
- at least one bio-ink extruder configured to eject the one or more bio-inks from the distal portion of the cannula; and
- a controller adapted:
  - to register a coordinate system of the surgical robot to a three-dimensional preoperative image set including three-dimensional preoperative images of the region of the subject, wherein a preoperative surgical plan for ejecting the one or more bio-inks is determined based on at least the three-dimensional preoperative image set;
  - to direct the surgical robot within the registered coordinate system to adjust a longitudinal position of the cannula and, using the surface opening as a pivot point, an orientation of the cannula within the subject in accordance with the preoperative surgical plan; and
  - to control the at least one bio-ink extruder such that the one or more bio-inks is ejected in accordance with the longitudinal position and the orientation of the cannula to form, within the subject, a three-dimensional tissue element having dimensions larger than the first lateral dimensions.

* * * * *